(12) United States Patent
Subramanian et al.

(10) Patent No.: US 12,325,523 B2
(45) Date of Patent: Jun. 10, 2025

(54) SELF-DISINFECTING PORTABLE PHYSICAL PARTITIONS FOR AIRCRAFT INTERIORS

(71) Applicant: B/E Aerospace, Inc., Winston-Salem, NC (US)

(72) Inventors: Sanith Kurumpilavu Subramanian, Bangalore (IN); Raja Mandava, Rammurthy Nagar (IN); Dharamveer Surya Prakash Bathla, Sonipat (IN)

(73) Assignee: B/E Aerospace, Inc., Winston-Salem, NC (US)

( * ) Notice: Subject to any disclaimer, the term of this patent is extended or adjusted under 35 U.S.C. 154(b) by 967 days.

(21) Appl. No.: 17/340,451

(22) Filed: Jun. 7, 2021

(65) Prior Publication Data
US 2021/0387729 A1 Dec. 16, 2021

(30) Foreign Application Priority Data
Jun. 12, 2020 (IN) .............................. 202011024785

(51) Int. Cl.
*B64D 11/06* (2006.01)
*A61L 2/10* (2006.01)
*B64F 5/30* (2017.01)

(52) U.S. Cl.
CPC ............ *B64D 11/0606* (2014.12); *A61L 2/10* (2013.01); *B64F 5/30* (2017.01); *A61L 2202/11* (2013.01);
(Continued)

(58) Field of Classification Search
CPC .......... B64D 11/0606; A61L 2/10; A61L 9/18; A61L 9/20; B64F 5/30
See application file for complete search history.

(56) References Cited

U.S. PATENT DOCUMENTS

| 4,825,921 A | 5/1989 | Rigter |
| 10,322,197 B1 * | 6/2019 | Williams .................. A61L 9/20 |

(Continued)

FOREIGN PATENT DOCUMENTS

| CN | 107165566 A | 9/2017 |
| DE | 202020101029 U1 | 3/2020 |

(Continued)

OTHER PUBLICATIONS

Extended Search Report in European Application No. 21179049.8, dated Feb. 11, 2022, 12 pages.

*Primary Examiner* — Regina M Yoo
(74) *Attorney, Agent, or Firm* — Suiter Swantz IP

(57) ABSTRACT

A self-disinfecting partition system is disclosed. The system includes a housing, and an attachment element configured to attach the housing to a surface. The system further includes one or more arms configured to deploy from a stored position an extended position. The system further includes a flexible screen coupled to the one or more arms configured to restrict a transmission of microbes. The system further includes a retraction assembly configured to retract the flexible screen into the housing. The system further includes an electromagnetic energy source disposed within the housing configured to emits disinfecting electromagnetic energy onto the flexible screen. A second self-disinfecting partition system is disclosed that includes a housing configured to fit around the headrest and/or seatback of a passenger seat. The system further includes an accordion-folded flexible screen coupled to the housing that deploys from the housing and disinfected via electromagnetic energy.

9 Claims, 14 Drawing Sheets

(52) U.S. Cl.
CPC ... *A61L 2202/121* (2013.01); *A61L 2202/122* (2013.01); *A61L 2202/123* (2013.01); *A61L 2202/26* (2013.01)

(56) References Cited

U.S. PATENT DOCUMENTS

| | | | |
|---|---|---|---|
| 10,413,622 B2 | 9/2019 | MacKin | |
| 10,494,101 B2 * | 12/2019 | Wilson | B64D 11/0642 |
| 2005/0194827 A1 * | 9/2005 | Dowty | B60N 3/06 297/411.3 |
| 2014/0077520 A1 * | 3/2014 | Mcmanus | B64D 11/0023 296/97.3 |
| 2015/0034843 A1 | 2/2015 | Antoniazzi | |
| 2017/0224855 A1 | 8/2017 | MacKin | |
| 2020/0331611 A1 | 10/2020 | Hack et al. | |

FOREIGN PATENT DOCUMENTS

| | | |
|---|---|---|
| FR | 2228652 A1 | 12/1974 |
| KR | 102162264 B1 | 10/2020 |
| WO | 2020039236 A1 | 2/2020 |

* cited by examiner

SELF-DISINFECTING PORTABLE PHYSICAL PARTITIONS FOR AIRCRAFT INTERIORS

PRIORITY

The present application claims the benefit under 35 U.S.C. § 119(e) of Indian Provisional App. No. 202011024785 (filed Jun. 12, 2020), entitled "SELF-DISINFECTING PORTABLE PHYSICAL PARTITIONS FOR AIRCRAFT INTERIORS (SEATING SYSTEM)", which is incorporated herein by reference in its entirety.

BACKGROUND

The transfer of microbes (e.g., virus, bacteria, or fungus) from person to person has become a greater concern over time due to recent pandemics. The commercial aircraft industry is particularly concerned about person-to-person transfer of microbes, as flight in an aircraft often necessitates congregating diverse groups of people in a constricted area for long periods of time.

To reduce the risk of transmission, barriers may be implemented between passengers to block or reduce microbial transfer. However, these barriers need to be disinfected often. The disinfection of these barriers often includes manual spraying and wiping surfaces with disinfection solution, a method that is time consuming, and may use toxic materials that may degrade aircraft interior surfaces over time. Accordingly, it is desirable to provide a system that avoids the shortcomings of conventional approaches.

SUMMARY

A self-disinfecting partition system is disclosed. In one or more embodiments, the self-disinfecting partition system includes a housing. In one or more embodiments, the housing includes an attachment element configured to attach the housing to a first surface. In one or more embodiments, the housing further includes an opening. In one or more embodiments, the self-disinfecting partition system further includes a flexible screen configured to restrict a transmission of microbes, and further configured to deploy from a retracted position within the housing to a deployed position at least partially outside of the opening. In one or more embodiments, the self-disinfecting partition system further includes a first arm mechanically coupled to an interior of the housing and configured to deploy from a first stored position within the housing to a first extended position at least partially outside of the opening. In one or more embodiments, the first arm includes a first screen attachment assembly coupled to a first end of the one arm, wherein the first end of the one arm is configured to attach to a first border of the flexible screen. In one or more embodiments, the self-disinfecting partition system further includes a retraction assembly configured to retract the flexible screen from the deployed position to the retracted position. In one or more embodiments, the retraction assembly includes a reel configured to wind the flexible screen. In one or more embodiments, the retraction assembly further includes one or more guide rollers configured to guide the flexible screen onto the reel. In one or more embodiments, the self-disinfecting partition system further includes an electromagnetic energy source disposed within the housing configured to emit electromagnetic energy onto the flexible screen, wherein the electromagnetic energy is configured to disinfect the flexible screen.

In some embodiments of the self-disinfecting partition system, the self-disinfecting partition system further includes a second arm mechanically coupled to the housing and configured to deploy from a second stored position within the housing to a second extended position at least partially outside of the housing. In some embodiments, the second arm includes a second screen attachment assembly coupled to a first end of the second arm, wherein the first end of the second arm is configured to attach to the first border of the flexible screen.

In some embodiments of the self-disinfecting partition system, the first arm is further configured to telescope.

In some embodiments of the self-disinfecting partition system, the first screen attachment assembly is in constant contact with the first border of the flexible screen as the flexible screen is deployed from the retracted position to the deployed position.

In some embodiments of the self-disinfecting partition system, the self-disinfecting partition system, further includes a connecting rod attached to the first screen attachment assembly and the second attachment assembly, wherein the connecting rod is coupled to the first border of the flexible screen.

In some embodiments of the self-disinfecting partition system, the self-disinfecting partition system further includes at least one door coupled to the housing configured to cover the opening when the first arm is retracted inside the housing.

In some embodiments of the self-disinfecting partition system, the first arm is further configured to rotate from a stored position to the extended position via a first joint.

In some embodiments of the self-disinfecting partition system, the first screen attachment assembly further includes a first screen clamp coupled to the flexible screen and slidably coupled to the first arm.

In some embodiments of the self-disinfecting partition system, the retraction assembly further comprises a rotary actuator configured to rotate the reel.

In some embodiments of the self-disinfecting partition system, the self-disinfecting partition system further comprises an electrical scheme configured to power at least one of the electromagnetic energy source or the retraction assembly.

In some embodiments of the self-disinfecting partition system, the self-disinfecting partition system further comprises a user interface communicatively coupled to the electrical scheme.

Another self-disinfecting partition system is disclosed. In one or more embodiments, the self-disinfecting partition system includes a housing. In one or more embodiments, the self-disinfecting partition system further includes an attachment element configured to couple the self-disinfecting partition system to the seat. In one or more embodiments, the attachment element includes one or more apertures configured to accept one or more supports. In one or more embodiments, the self-disinfecting partition system further includes an extension assembly coupled to the housing and the attachment element. In one or more embodiments, the extension assembly includes the one or more supports coupled to the housing and configured to slide within the one or more apertures, wherein sliding of the one or more supports within the one or more apertures adjusts a distance of the housing from the seat. In one or more embodiments, the extension assembly further includes a lock coupled to the attachment element and operationally coupled to the one or more supports and the one or more apertures; wherein the lock is configured upon activation to restrict a movement of the one or more supports relative to the one or more apertures. In one or more embodiments, the self-disinfecting partition system further includes a flexible screen configured to block a transmission of microbes, and further configured to deploy from a retracted position within the housing to a deployed position. In one or more embodiments, the self-disinfecting partition system further includes one or more electromagnetic energy sources disposed within the housing configured to emit electromagnetic energy onto the flexible screen when the flexible screen is configured in the retracted position, wherein the electromagnetic energy is configured to disinfect the flexible screen.

In some embodiments of the self-disinfecting partition system, the flexible screen is configured to retract via an accordion fold.

In some embodiments of the self-disinfecting partition system, the self-disinfecting partition system further includes an electrical scheme configured to power at least one of the electromagnetic energy source.

In some embodiments of the self-disinfecting partition system, the self-disinfecting partition system further includes a user interface communicatively coupled to the electrical scheme.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION

Figure 1A:
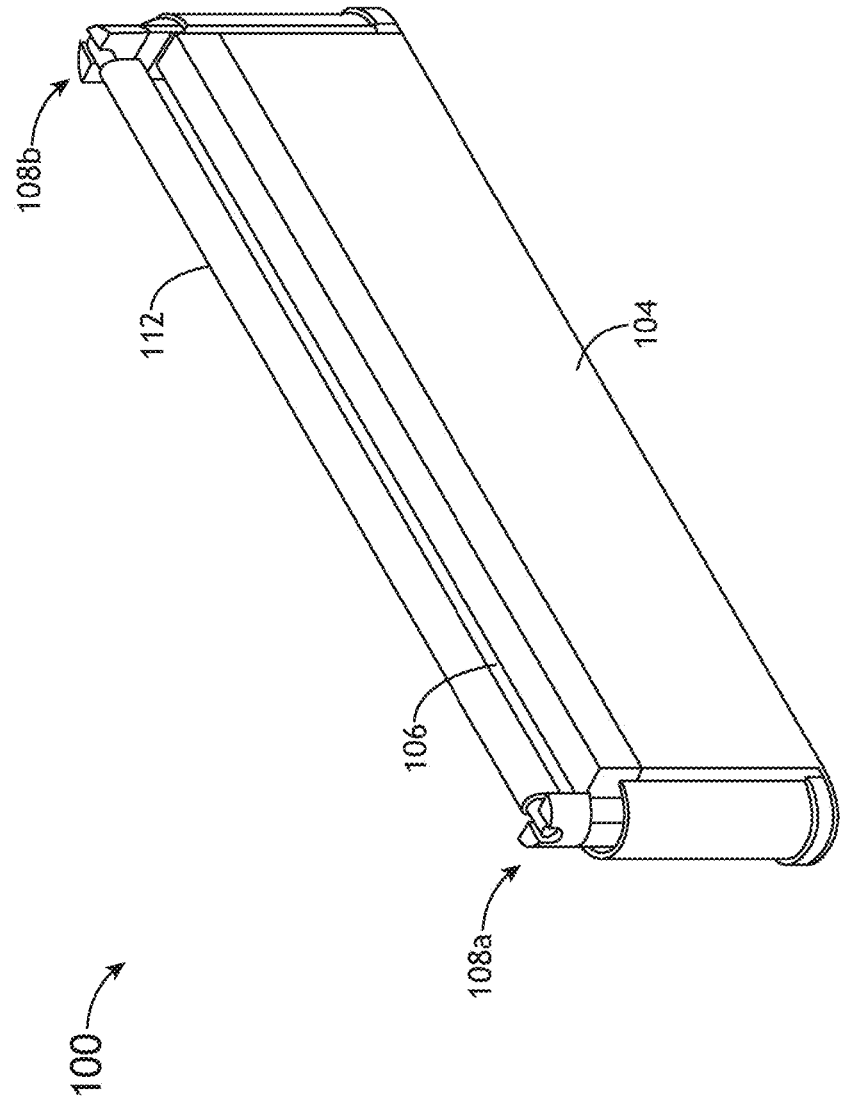
FIG. 1A is a perspective view of a self-disinfecting partition system configured in a retracted position, in accordance with one or more embodiments of the disclosure.

Before explaining one or more embodiments of the disclosure in detail, it is to be understood that the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of sub-combination of two or more such features, along with any other features which may not necessarily be expressly described or inherently present in the instant disclosure.

A self-disinfecting partition system is disclosed. The self-disinfecting partition system may be used to prevent communication of microbes between people, such as passengers on an aircraft, via a deployable partition screen that retracts from a housing. When not in use, the partition screen may be retracted into the housing. Electromagnetic energy (e.g., ultraviolet light) scanners within the housing scan the partition screen while the partition screen is retracting and/or retracted, sterilizing microbes that have attached themselves to the screen.

FIG. 1A is a perspective view of a self-disinfecting partition system 100 configured in a retracted position, in accordance with one or more embodiments of the disclosure. The self-disinfecting partition system 100 is configured to configured to block, or otherwise hinder, the transmission of pathogens (e.g., bacteria, viruses, or fungi) from one person to another. The self-disinfecting partition system 100 may be configured for use in a wide variety of environments including but not limited to vehicles (e.g., aircraft, buses, trains, taxis) medical reception areas, ticket counters, payment terminals (e.g., at supermarkets), movie theaters and other public venues. For example, the self-disinfecting partition system 100 may be configured for use on a passenger seat of a commercial aircraft.

In embodiments, the self-disinfecting partition system 100 includes a housing 104 that houses one or more components of the self-disinfecting partition system 100. The housing 104 may be configured of any shape of form including but not limited to a rectangular prism. self-disinfecting partition system 100 further includes a flexible screen 106 (e.g., mostly hidden from view in FIG. 1A). The flexible screen 106 is stored in a retracted position within the housing 104 when not in use (e.g., as in FIG. 1A), then subsequently extended into a deployed position when in (e.g., as in FIG. 1B). The flexible screen 106 may be of any size of shape, and may be constructed of any material included but limited to cloth, fiber, nylon, or plastic.

In some embodiments, the self-disinfecting partition system 100 further includes a first screen attachment assembly 108a and/or a second screen attachment assembly 108b configured to attach to a first border of the flexible screen 106. The first border of the flexible screen 106 may be considered a strip of a relatively small width (e.g., approximately 2 cm) of the leading edge of the flexible screen 106. The first screen attachment assembly 108a and/or a second screen attachment assembly 108b may use any type of technology to attach to the first border of the flexible screen including but not limited the use of clamps, adhesives, and crimping.

In some embodiments, the first screen attachment assembly 108a and/or the second screen attachment assembly 108b further includes a connecting rod 112 coupled to the first screen attachment assembly 108a and the second screen attachment assembly 108b (e.g., the connecting rod provides the major attachment point of the flexible screen 106 and acts as an extension of the first screen attachment assembly 108a and/or the second screen attachment assembly 108b.) The connecting rod 112 may be attached to the first screen attachment assembly 108a and/or the second screen attachment assembly 108b using any technology including but not limited to a bushing.

Figure 1B:
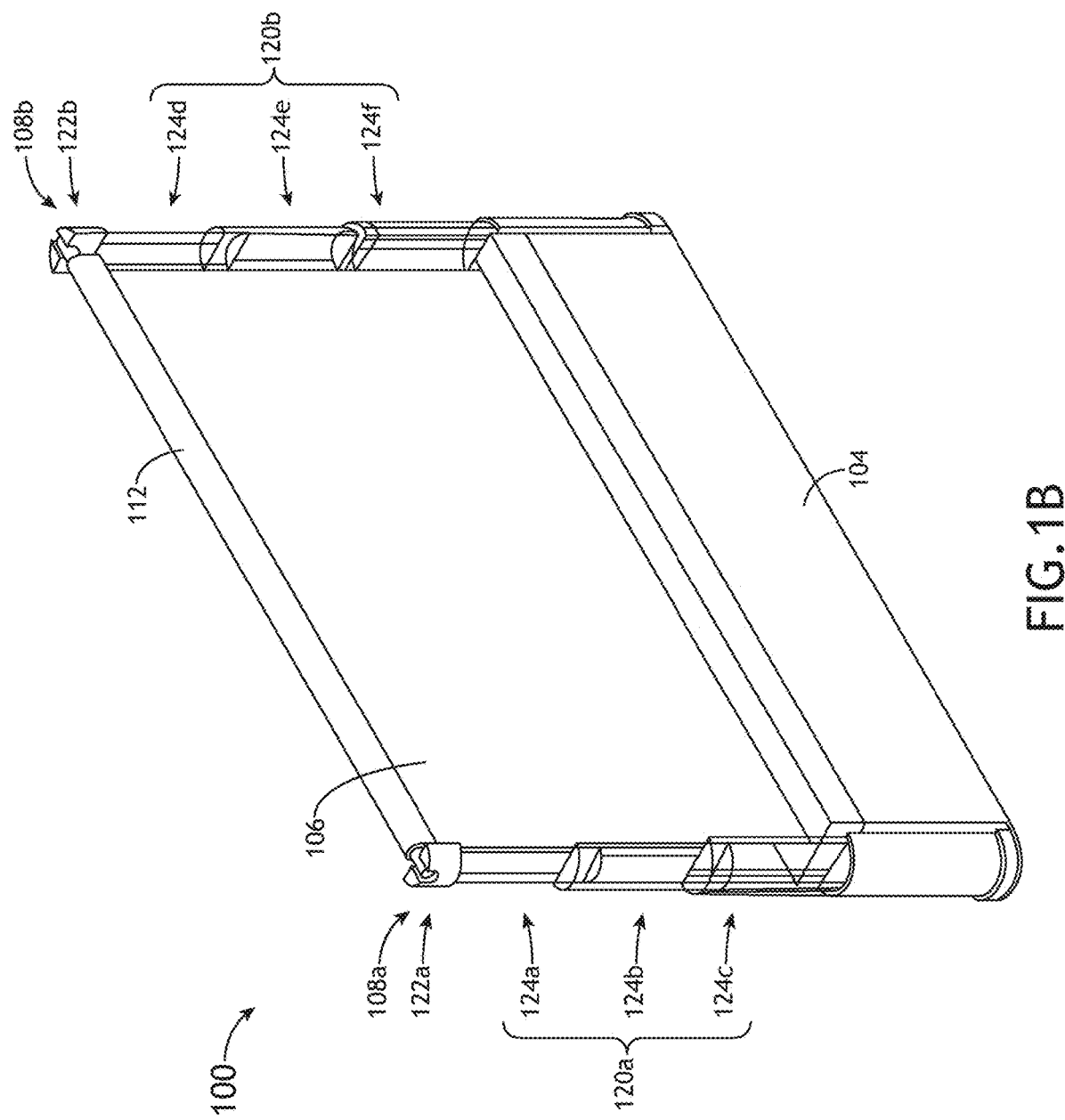
FIG. 1B is a perspective view of a self-disinfecting partition system with the flexible screen extended in a deployed configuration, in accordance with one or more embodiments of the disclosure.

FIG. 1B is a perspective view of a self-disinfecting partition system 100 with the flexible screen 106 extended in a deployed configuration, in accordance with one or more embodiments of the disclosure. The extension of the flexible screen may be accomplished by manually pulling upwards on the connecting rod. In some embodiments, the extension of the flexible screen is accomplished through a rotary actuator disposed within the housing 104 (e.g., electrically powered, or powered by a spring).

The extension of the flexible screen 106 from the housing 104 exposes a first arm 120a and a second arm 120b that rise from the housing 104 to support the flexible screen. For example, a first end of the first arm 120 may be coupled to the first screen attachment assembly 108a, whereas a second end 122b of the second arm may be attached to the second screen attachment assembly 108b. In some embodiments, the first arm 120a and/or second arm 120b may be configured with telescopic subunits 124a-f, allowing the first arm 120a and/or second arm 120b to straightforwardly extend and/or retract into the housing 104. In this manner, the screen attachment assemblies 108a, 108b (e.g., including the connecting rod 112) are in constant contact with the first border of the flexible screen 106 as the flexible screen 106 is deployed from the retracted position to the deployed position.

Figure 2:
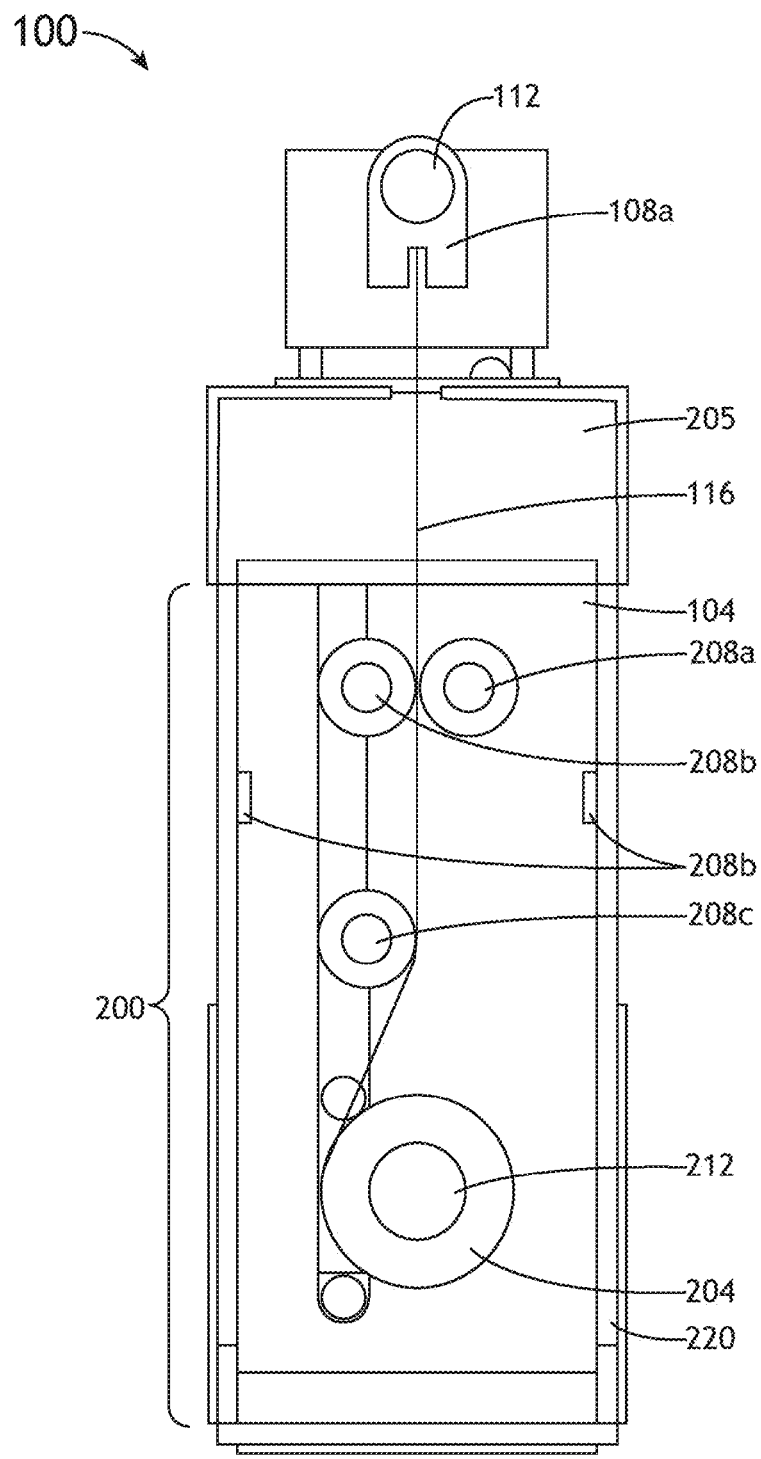
FIG. 2 is a side cutaway view of the self-disinfecting partition system configured in a retracted position, in accordance with one or more embodiments of the disclosure.

FIG. 2 is a side cutaway view of the self-disinfecting partition system 100 configured in a retracted position, in accordance with one or more embodiments of the disclosure. In some embodiments, the self-disinfecting partition system 100 further includes a retraction assembly 200 configured to guide and/or power the flexible screen 106 into the housing 104. The retraction assembly 200 may include a reel 204 attached to an end border of the flexible screen 106 (e.g., the border of the flexible screen 116 opposite of the first border). Upon retraction of the flexible screen 106, the reel 204 may actuate via a rotary actuator 212 (e.g., a loaded spring or electric motor), effectively winding the flexible screen 106 upon the reel 204.

In some embodiments, the retraction assembly further includes one or more guide rollers 208a-c configured to guide the flexible screen 106 onto the reel 204. For example, a pair of guide rollers 208a, 208b may be closely positioned on opposite surfaces of the flexible screen 106, acting to guide the flexible screen 106 toward the reel 204 and/or provide facilitate a tension upon the flexible screen 106 so that the flexible screen 106 may be properly wound.

In some embodiments, the housing further includes one or more electromagnetic energy sources 216 configured to emit electromagnetic energy onto the flexible screen 106. The one or more electromagnetic energy sources 216 may emit any type of electromagnetic energy that disinfects/sterilized the flexible screen 106 including but not limited to ultraviolet light and X-rays. For example, the electromagnetic energy sources 216 may include any type or form of ultraviolet light-emitting technology including but not limited to light-emitting diodes (LED), mercury vapor lights, shortwave fluorescent lamp tubes, "black light" incandescent lamps, gas-discharge lamps, and lasers. For example, one or more electromagnetic energy sources 216 may be configured as an ultraviolet-emitting LED. The self-disinfecting partition system 100 may use any number, size, type, or configuration of the one or more electromagnetic energy sources 216. For example, the housing may include two lines of ultraviolet-emitting LEDs that run along opposing interior sides of the housing 104.

In some embodiments, the one or more electromagnetic energy sources 216 emit electromagnetic energy only while the flexible screen is being retracted or deployed. In some embodiments, the electromagnetic energy sources 2016 emit electromagnetic energy while flexible screen has been fully deployed (e.g., for a set amount of time).

In some embodiments, the housing 104 may include one or more attachment elements 220 configured to attach the housing 104 to a surface (e.g., the surface of a chair, armrest, setback, headrest, overhead bin, or side console). The one or more attachment elements 220 may including any type of attachment technology including but limited to adhesives, bolts, screws, hook-and-loop, suction or an interference fit. In some embodiments, the housing further includes a cap 205.

Figure 3A:
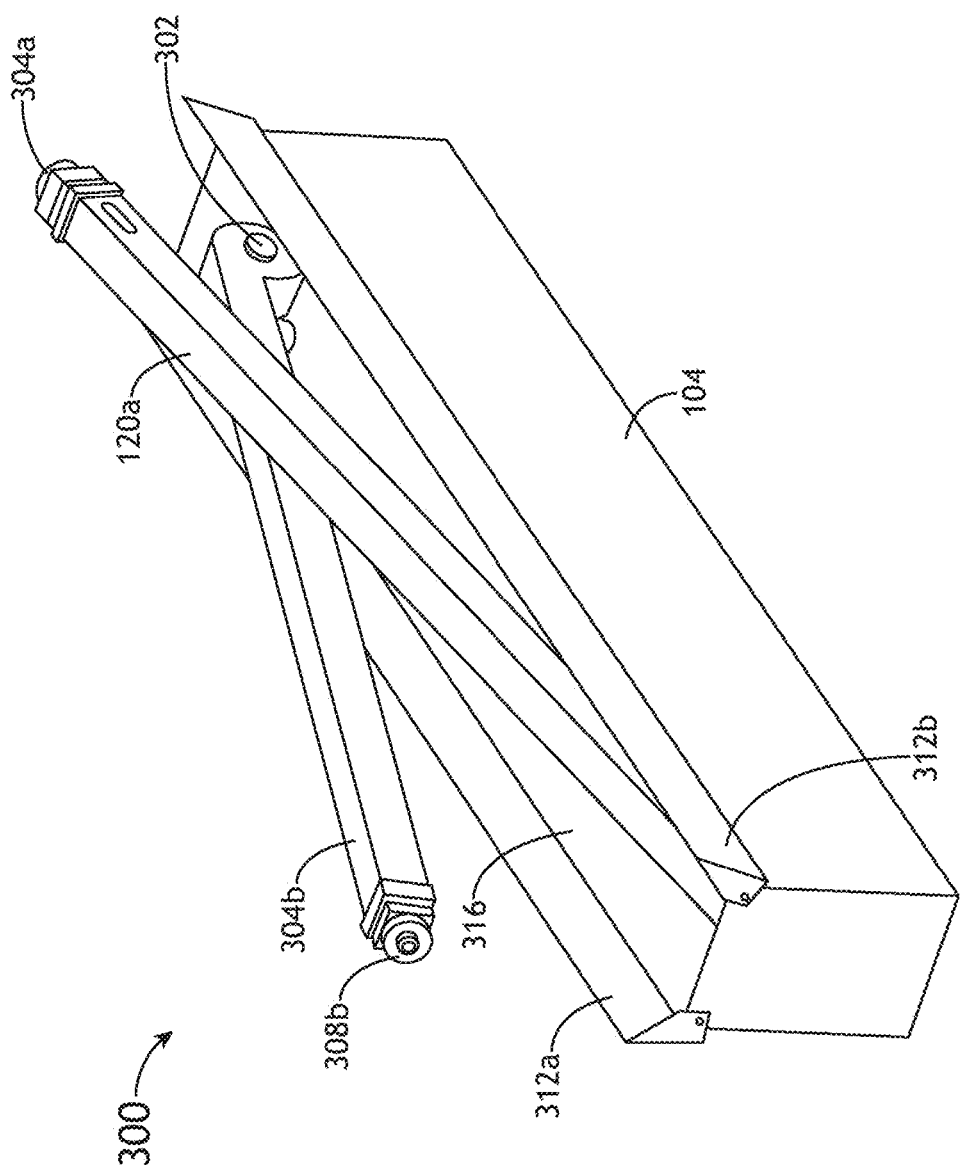
FIG. 3A is a perspective view of a self-disinfecting partition system configured in a partially deployed position, in accordance with one or more embodiments of the disclosure.
Figure 3B:
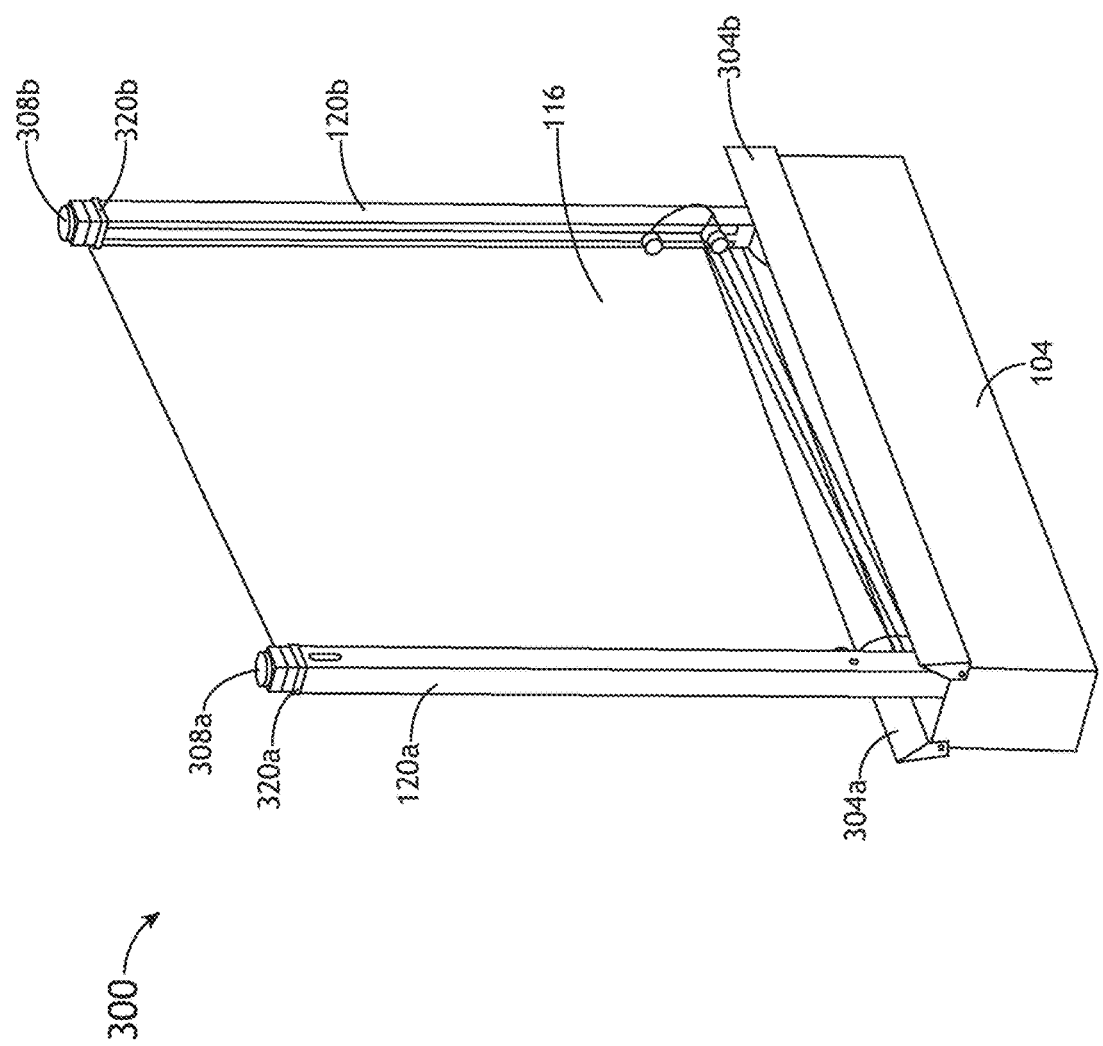
FIG. 3B is a perspective view of a self-disinfecting partition system 300 configured in a partially deployed position, in accordance with one or more embodiments of the disclosure.

FIG. 3A is a perspective view of a self-disinfecting partition system 300 configured in a partially deployed position, in accordance with one or more embodiments of the disclosure. The self-disinfecting partition system 300 may include one or more, or all, components of the self-disinfecting partition system 100, and vice versa. In some embodiments, the first arm 304a and/or second arm 304b self-disinfecting partition system 300 are configured to rotate or swing out from the housing 104 into a first extended position via a joint 302 (e.g., only visible for the second arm 304b) operationally coupled to the housing 104. The first arm 304a and/or second arm 304b may be manually rotated or rotated via an actuator. In some embodiments of the self-disinfecting partition system 300, the flexible screen 106 includes a first screen attachment assembly 308a and/or a second screen attachment assembly 308b that attaches to the flexible screen 106 after the first arm 304a and/or the second arm 304b has been deployed (e.g., as shown in FIG. 3B). In some embodiments, the first arm 304a and/or the second arm 304b of the self-disinfecting partition system 300 may be further extended via telescopic subunits 124.

In some embodiments, the self-disinfecting partition system 300 further includes one or more doors 312a, 312b coupled to the housing 104 configured to cover an opening 316 of the housing. The one or more doors prevent the electromagnetic energy (e.g., ultraviolet light) from escaping the housing 104 when the flexible screen 106 is retracted. The one or more doors 312a, 312b may include any type of latching mechanism including but not limited to a spring latch. The one or more doors 312a, 312b may be configured so that the one or more electromagnetic energy source 216 will automatically shut off if the one or more doors is opened, preventing the transmission of potentially harmful electromagnetic energy to a person.

FIG. 3B is a perspective view of a self-disinfecting partition system 300 configured in a partially deployed position, in accordance with one or more embodiments of the disclosure. In some embodiments, the first screen attachment assembly 308a and/or a second screen attachment assembly 308b further includes a first screen clamp 320a and/or a second screen clamp 320b, respectively. The first screen clamp 320a and/or a second screen clamp 320b are coupled to the flexible screen (e.g., at the first border), and are slidably coupled to the first arm 304a and/or the second arm 304b, respectively. When the first arm 304a and/or the second arm 304b are deployed, the first screen clamp 320a and second screen clamp 320b may be slid from the bottom end of the first arm 304a and/or the second arm 304b to the top end of the first arm 304a and/or the second arm 304b, wherein the first screen clamp 320a and/or second screen clamp 320b may be slid next to, or attached (e.g., via an interference fit) to components of the first screen attachment assembly 308a and/or a second screen attachment assembly 308b. In this manner, the flexible screen 106 may be deployed back and forth from a retracted position to a deployed position (e.g., via the retraction assembly 200) and disinfected via the electromagnetic energy source 216.

Figure 4:
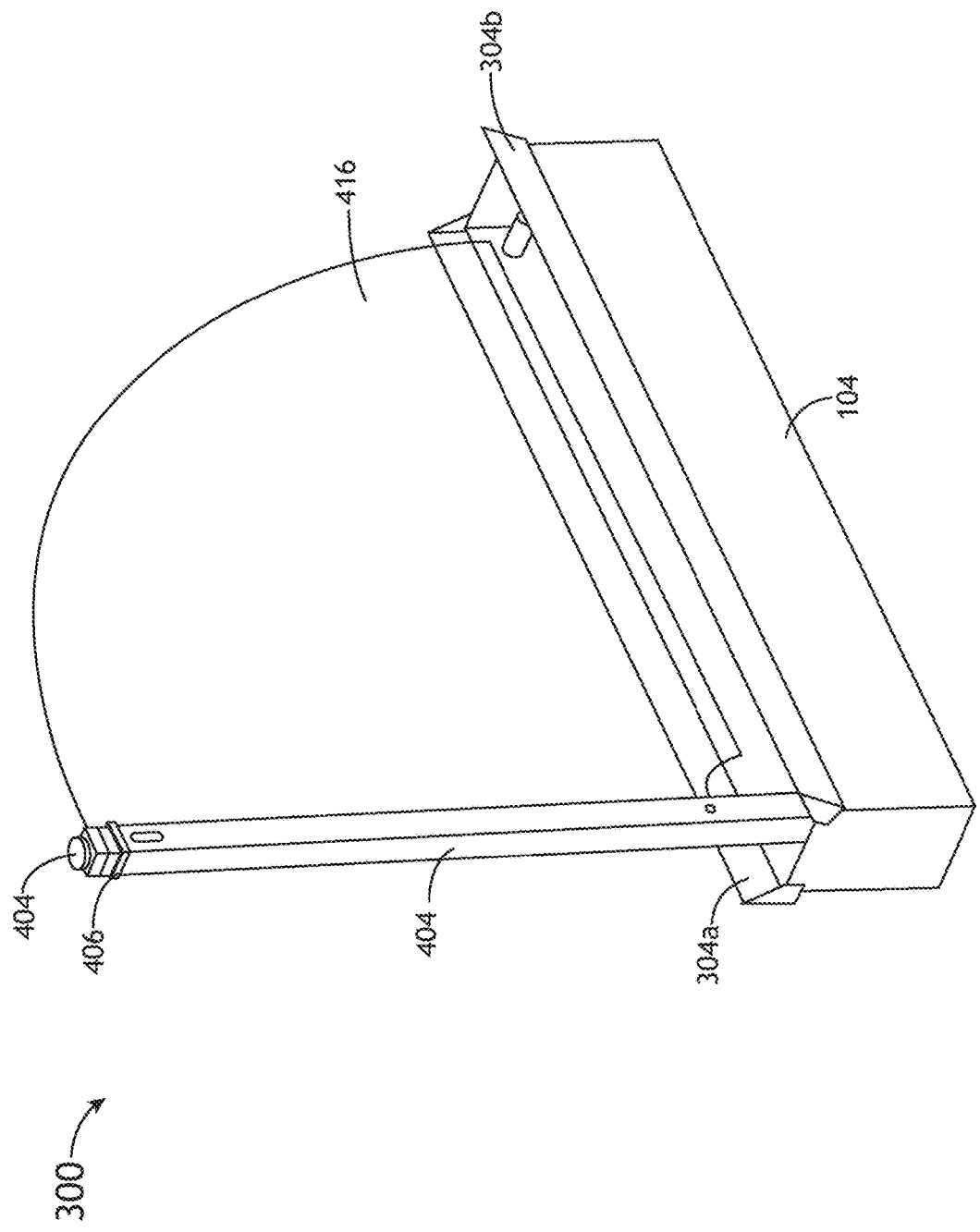
FIG. 4 is a perspective view of a self-disinfecting partition system configured in a partially deployed position, in accordance with one or more embodiments of the disclosure.

FIG. 4 is a perspective view of a self-disinfecting partition system 400 configured in a partially deployed position, in accordance with one or more embodiments of the disclosure. The self-disinfecting partition system 400 may include one or more, or all, components of self-disinfecting partition system 100, 300, and vice versa.

In some embodiments, the self-disinfecting partition system 400 is configured with only one arm 404 and a flexible screen 416 having a shape configured to retain a partition structure while being supported by the arm 404. For example, the flexible screen 106 may be configured as a curved partition, as in FIG. 4. In some embodiments, the arm 404 may be configured with one or more telescopic subunits 124 and telescope linearly into the housing. The arm may also be configured as a pivoting arm (e.g., configured with or without telescopic subunits 124) configured to pivot into the housing 104. In this manner, a screen attachment assembly 404 (e.g., a first screen assembly that includes a screen clamp 406 slidably coupled to the arm 404 and attached to the flexible screen 416, where sliding of the screen clamp 406 deploys the flexible screen 416 from a retracted to deployed position.

Figure 5:
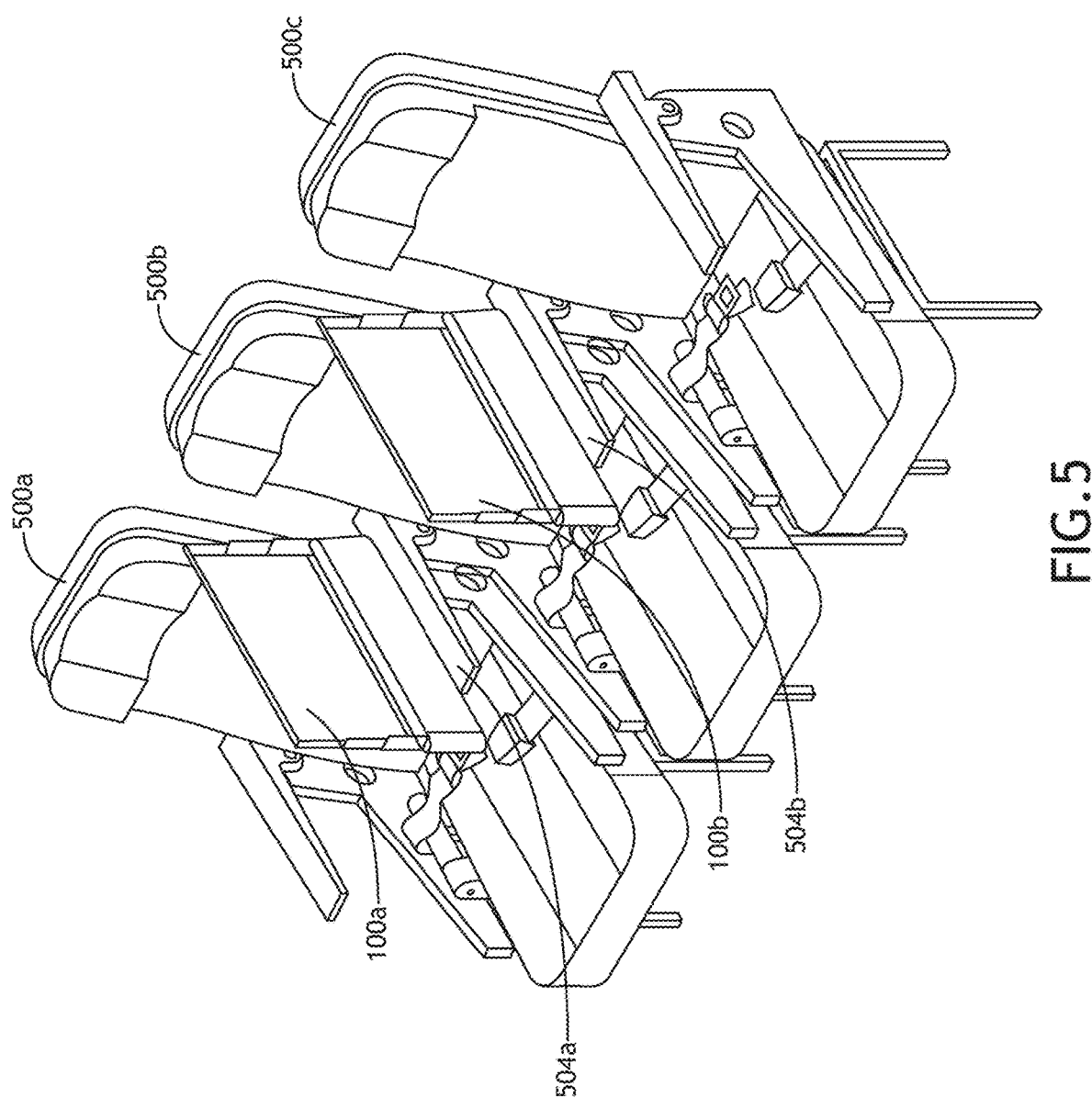
FIG. 5 is a drawing illustrating the attachment of two self-disinfecting partition systems a row of passenger seats in accordance with one or more embodiments of the disclosure.

FIG. 5 is a drawing illustrating the attachment of two self-disinfecting partition systems 100a-b to a row of passenger seats 500a-c in accordance with one or more embodiments of the disclosure. The self-disinfecting partition systems 100, 300, 400 may be attached to any surface on or around the one or more passenger seats 500a-c including but not limited to an armrest 500a-b, headrest, seatback, overheat pin, floor, console, or other structure or chair component disposed between passenger seats 500a-c.

The self-disinfecting partition systems 100, 300, 400 may be implemented in any orientation. For example, the self-disinfecting partition system 100, 300, 400 may be attached to a structure (e.g., armrest) configured so that the flexible screen 106 is pulled upward from the retracted position to the deployed position (e.g., as in FIG. 5). In another example, the self-disinfecting partition system 100, 300, 400 may be attached to an overhead structure (e.g., overhead storage or ceiling) configured so that the flexible screen 106 is pulled downward from the retracted position to the deployed position. In another example, the self-disinfecting partition systems 100, 300, 400 may be placed on an adjacent side (e.g., upon the armrest) and configured so that the flexible screen 106 is pulled in a side-to-side motion from the retracted position to the deployed position.

Figure 6A:
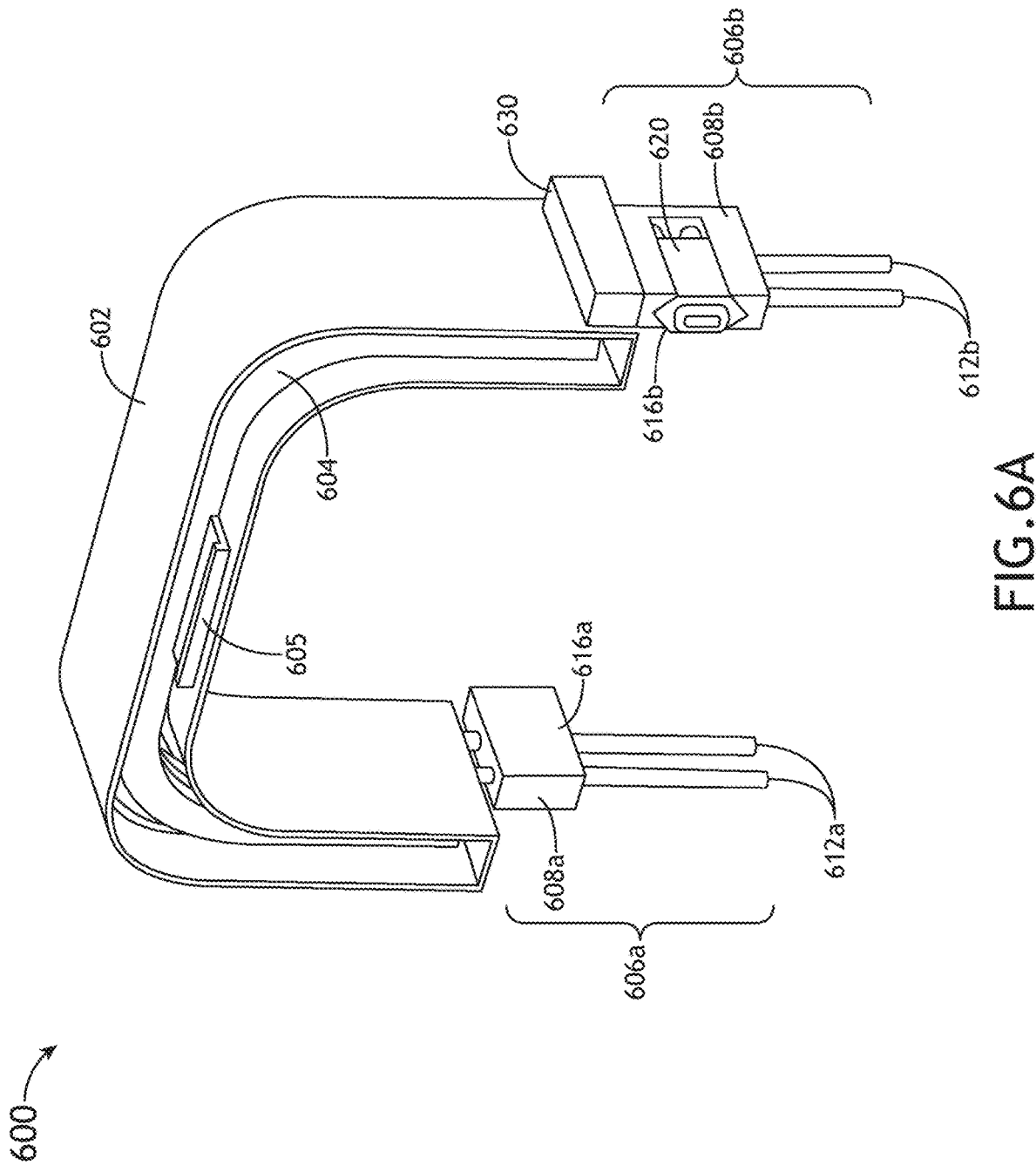
FIG. 6A is a perspective view of a self-disinfecting partition system configured in a retracted position, in accordance with one or more embodiments of the disclosure.
Figure 6B:
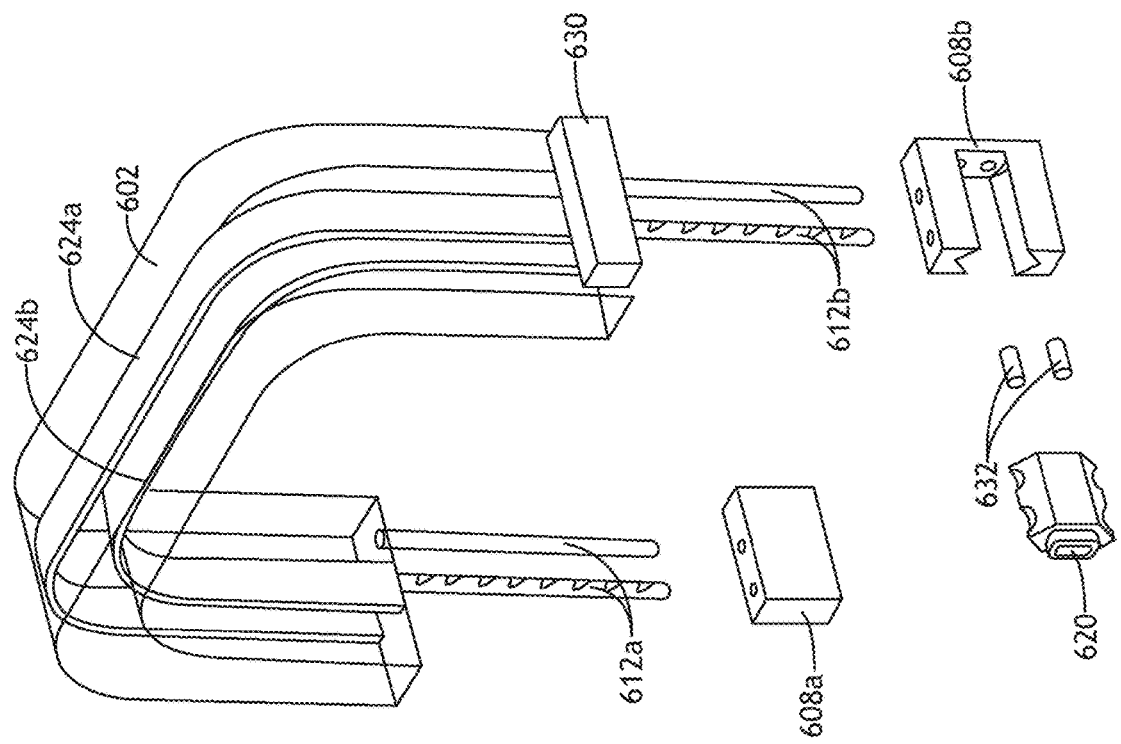
FIG. 6B is an exploded view of a self-disinfecting partition system configured in a retracted position, in accordance with one or more embodiments of the disclosure.
Figure 6B:
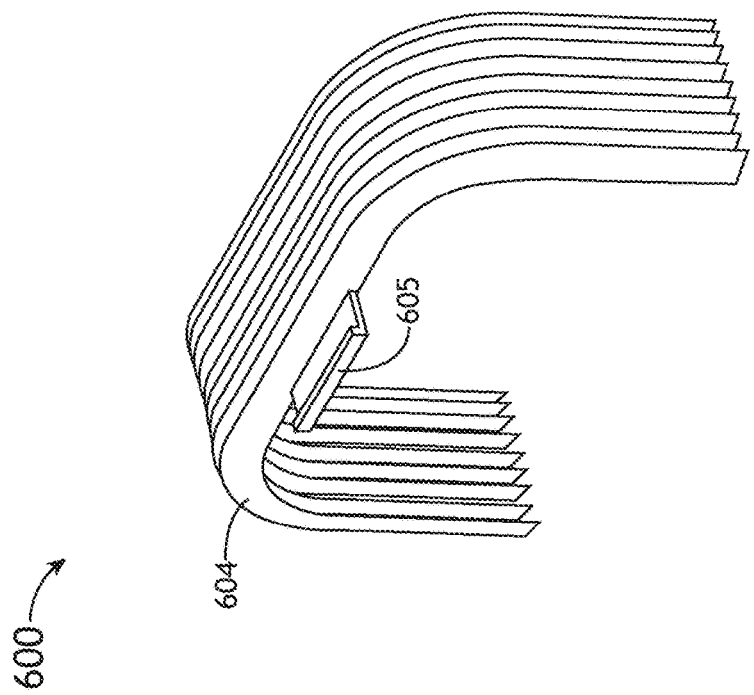

FIG. 6A and FIG. 6B are a perspective view and an exploded view, respectively, of a self-disinfecting partition system 600 configured in a retracted position, in accordance with one or more embodiments of the disclosure. The self-disinfecting partition system 600 may include one or more, or all, components of self-disinfecting partition system 100, 300, 400 and vice versa.

In some embodiments, the self-disinfecting partition system 600 includes a housing 602 configured to house a flexible screen 604. The housing 602 may be configured of any shape for form. For example, the housing may be shaped to fit around or over the headrest and/or seatback of a seat (e.g., a passenger seat 500). The flexible screen 604 may be configured with an accordion fold, facilitating the transition from an extended, deployed position to a stored, retracted position. The flexible screen 604 may include a handle 605, whereby a user may grab the handle 605 and manually extend and/or retract the flexible screen 604.

In some embodiments, the self-disinfecting partition system 600 further includes an extension assembly 606a, 606b configured to raise and lower the housing relative to the seat (e.g., adjust the distance of the housing 602 from the at least one of the headrest or the seatback of the passenger seat 500). The extension assembly 606a, 606b comprises one or more attachment elements 608a, 608b and one or more supports 612a, 612b coupled to the housing 602 and configured to insert and slide within one or more apertures (e.g., tracks or holes) formed within the attachment elements 608a, 608b (e.g., the one or more supports 612a, 612b are slidably coupled to the one or more attachment elements 608a, 608b, with the one or more apertures within the attachment elements 608a, 608b configured to accept one or more supports 612a, 612b). The one or more attachment elements 608a, 608b include one or more attachment surfaces 616a, 616b that may couple to any surface (e.g., the sides of a seatback of a seat) via any technology including but not limited to adhesive technology, bolts, screws, hook-and-loop, and suction. The one or more supports 612a, 612b may be of any shape or size and made of any material. Once the supports 612a, 612b are inserted within the one or more apertures within the seat-attached one or more attachment elements 612, the height of the housing 602 to be adjusted relative to the seat. For example, upon attachment of the self-disinfecting partition system 600 to a seat, a relatively tall person may pull upward on the housing 602 sliding the one or more supports 612a, 612, relative to the one or more attachment elements 608a, 608b, effectively raising the housing 602 so that the housing 602 will not interfere with the relatively tall person when seated.

In some embodiments, the self-disinfecting partition system 600 further includes a lock 620 coupled to one or more of the attachment elements 608a, 608b and configured to restrict the sliding of the one or more supports 612a, 612b, relative to the one or more attachment elements 608a, 608b. The lock 620 may be configured as any type of locking mechanism including but not limited to a friction lock, an interference lock, a clamp, a ratchet stay, and a tightening screw (e.g., with a friction fitting). For example, the lock 620 may include a friction lock having a spring-loaded component (e.g., containing springs 632) that presses against one of the one or more supports 612a, 612b. The frictional force generated at the mating surface of the lock 620 and the one of the one or more supports 612a, 612b restricts movement of the housing to a set position. Adjustment of the lock 620 would then require manually pressing upon the lock in a fashion counter to the pressure of the supplied by the spring-loaded component, which reduces the friction applied by the lock 620, allowing the height of the housing to be adjusted.

In some embodiments, the self-disinfecting partition system 600 further includes one or more electromagnetic energy units 624a, 624b configured to deliver disinfecting amounts of electromagnetic energy. For example, the self-disinfecting partition system 600 may be configured with electromagnetic energy units 624a, 624b disposed on both sides of the flexible screen. The self-disinfecting partition system 100, 300, 400, 600 may further include a battery 630 configured to power the electromagnetic energy units 624a, 624b and or the retraction assembly 200. In some embodiments, the self-disinfecting partition system 100, 300, 400, 600 is powered by an external power source.

Figure 7:
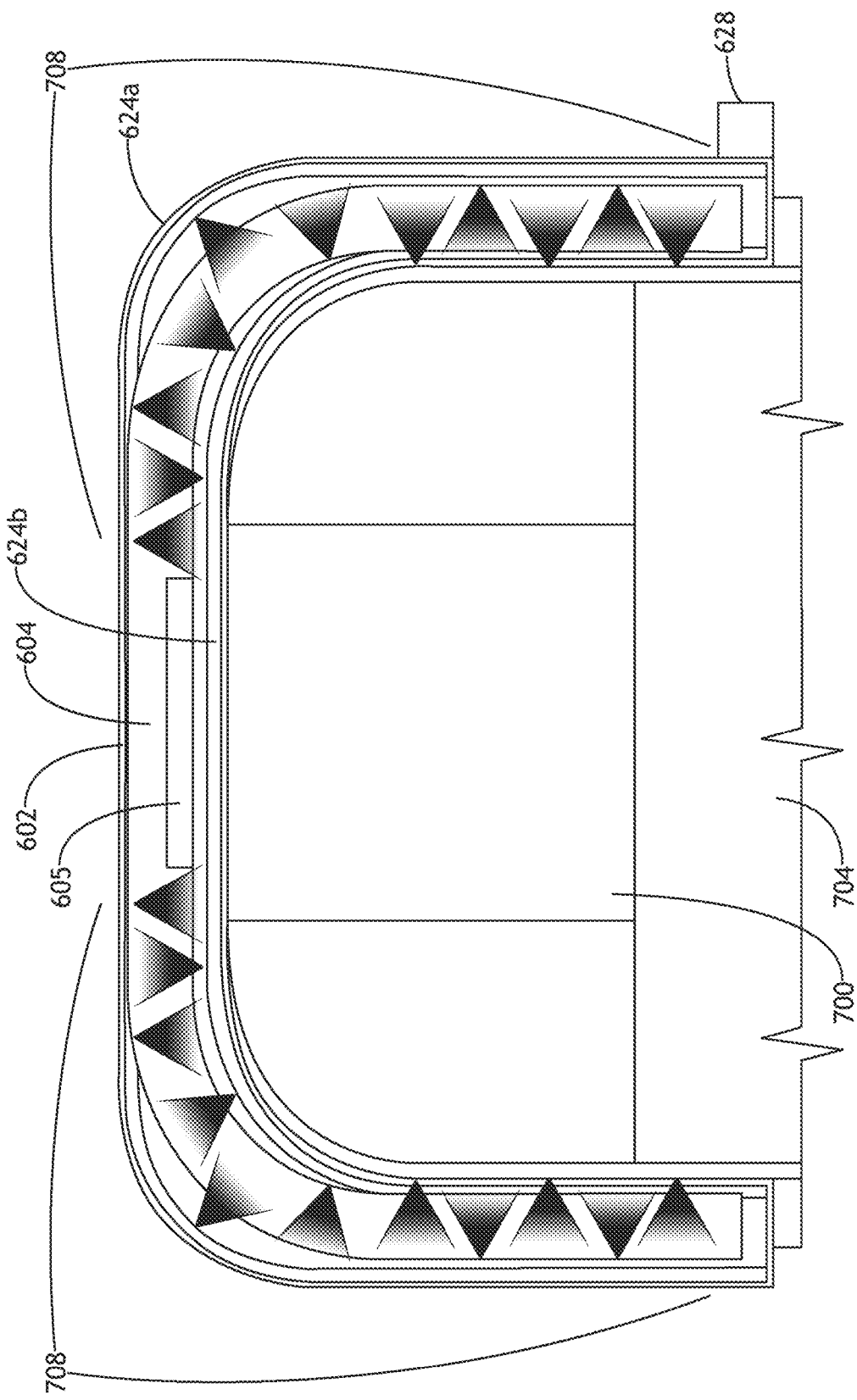
FIG. 7 illustrates a close-up front view of the housing of the self-disinfecting partition system configured in a retracted position, in accordance with one or more embodiments of the disclosure.

FIG. 7 illustrates a close-up front view of the housing 602 of the self-disinfecting partition system 600 configured in a retracted position, in accordance with one or more embodiments of the disclosure. The housing 602 is shown closely conforming to a headrest 700 and a seatback 702 of a passenger seat 500. The electromagnetic energy units 624a, 624b are disposed on opposite sides of the retracted and folded flexible screen 604. Each electromagnetic energy unit 624a, 624b contains one or more electromagnetic energy sources 216. The electromagnetic energy sources 216 may be configured as any type electromagnetic energy and include any type or form of light-emitting technology as described herein. For example, the electromagnetic energy sources 216 may be arranged into clusters 708 as shown in FIG. 7.

Figure 8A:
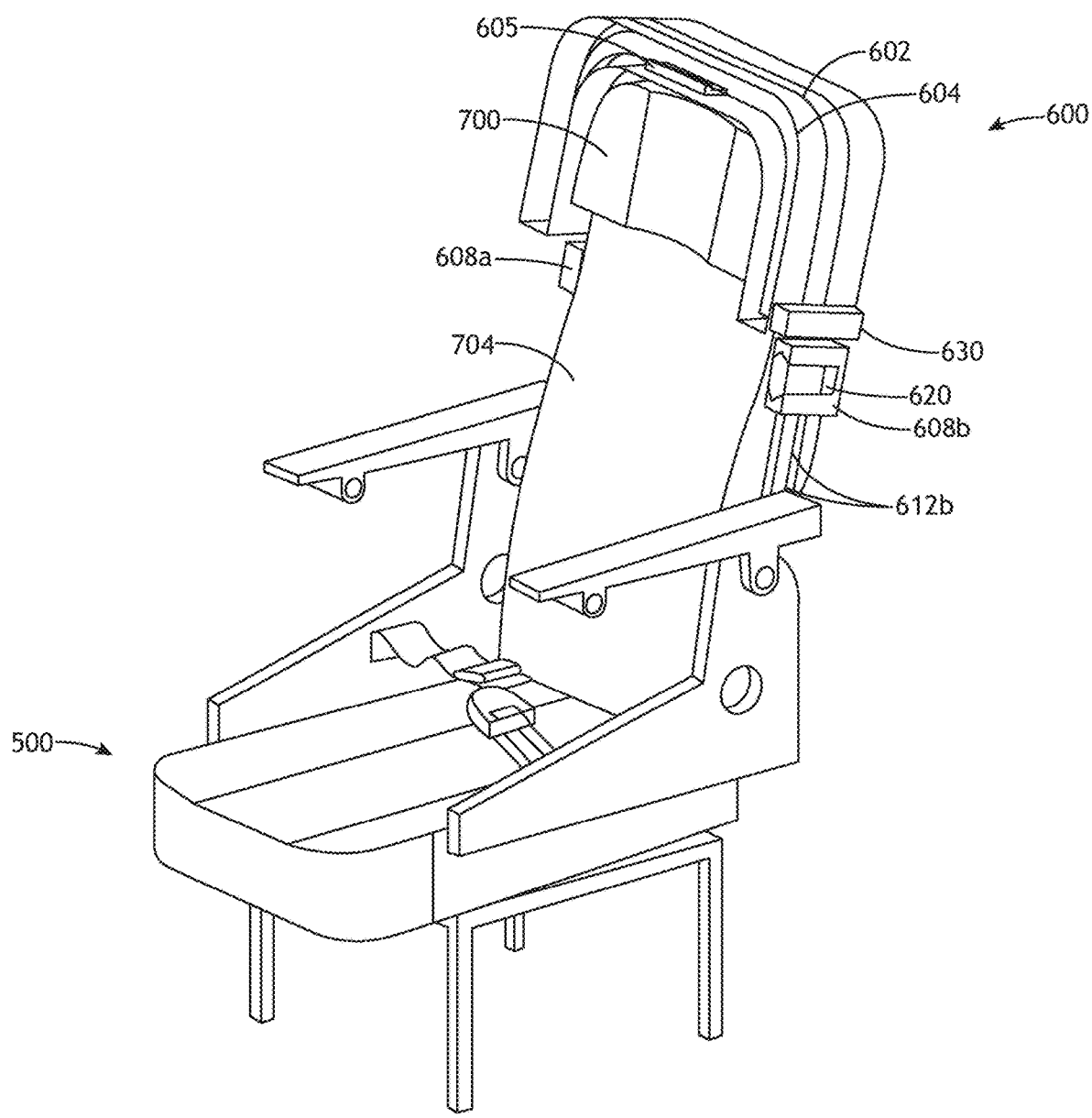
FIG. 8A illustrates a perspective view of the self-disinfecting partition system mounted on a passenger seat configured in a retracted position, in accordance with one or more embodiments of the disclosure.
Figure 8B:
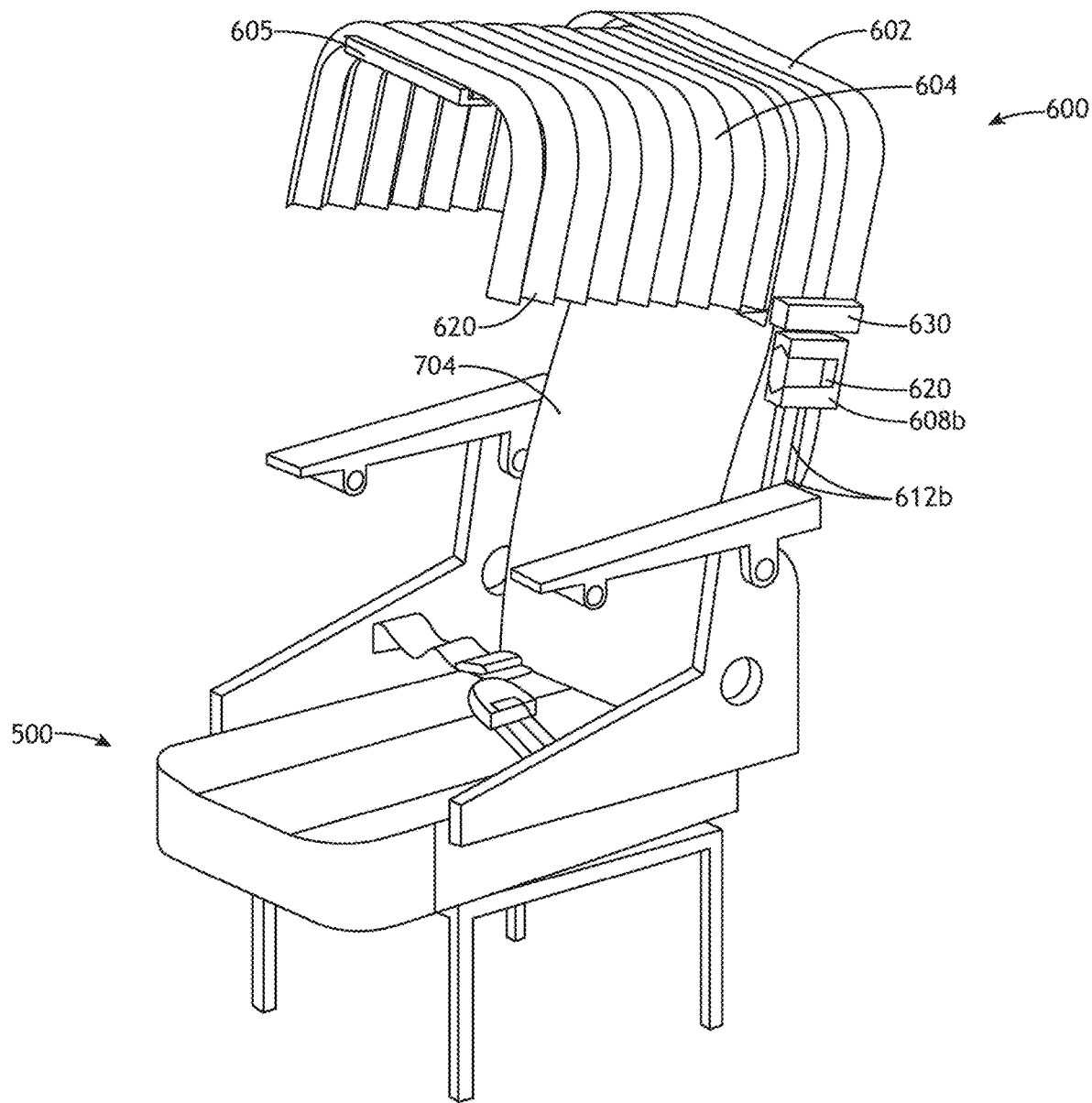
FIG. 8B illustrates a perspective view of the self-disinfecting partition system mounted on a passenger seat configured in a deployed position, in accordance with one or more embodiments of the disclosure.

FIG. 8A and FIG. 8B illustrate perspective views of the self-disinfecting partition system 600 mounted on a passenger seat 500 configured in a retracted and deployed positions, respectively, in accordance with one or more embodiments of the disclosure. With the flexible screen 604 retracted, a passenger may easily access, sit down, and/or leave from the passenger seat 500. When sitting in the passenger seat 500, the passenger can freely deploy or retract the flexible screen 604 by pulling or pushing on the handle 605.

Figure 9A:
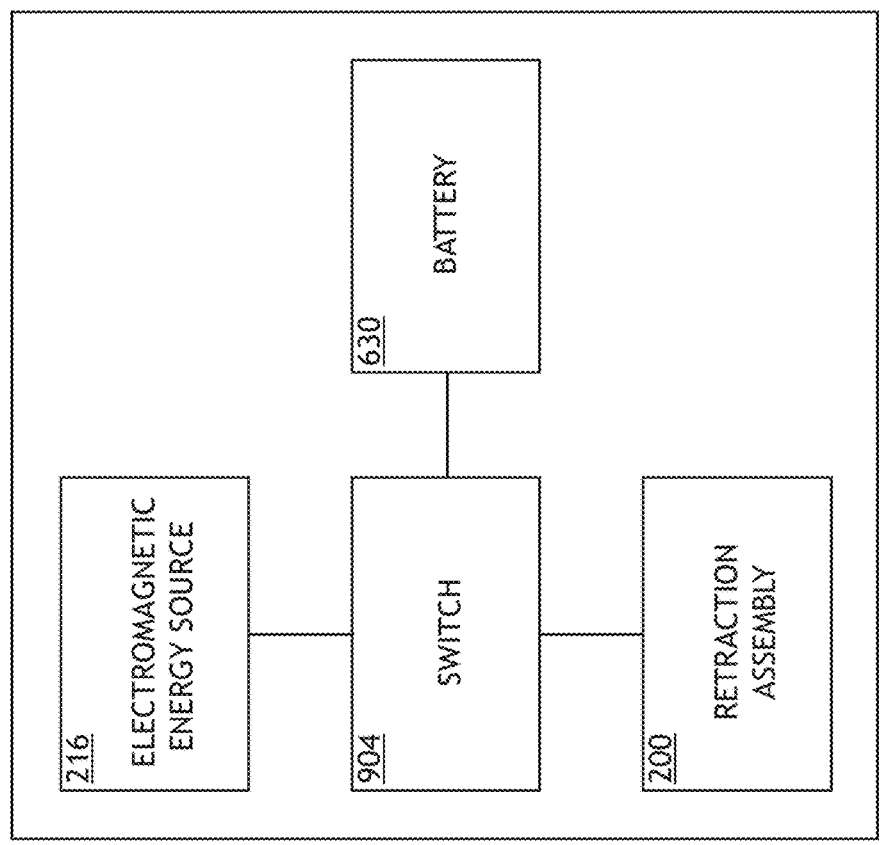
FIG. 9A is a block diagram illustrating an electrical scheme within the self-disinfecting partition system, in accordance with one or more embodiments of the disclosure.

The self-disinfecting partition system 100, 300, 400, 600 may further include any type of electrical system or scheme configured to power the one or more electromagnetic energy sources 216 and/or the retraction assembly. FIG. 9A is a block diagram illustrating an electrical scheme 900 within the self-disinfecting partition system 100, 300, 400, 600, in accordance with one or more embodiments of the disclosure. In an example, electrical scheme 900 may include the battery 630, the one or more electrical energy sources 216, and one or more switches 904. For instance, the electrical scheme 900 may include a switch 904 that is manually or automatically turned to an OFF or ON position, regulating the flow of electricity to power the one or more electromagnetic energy source 216. In another example, the electrical scheme may further include a switch 904 that is manually or automatically operated to activate or inactivate the retraction assembly 200.

Figure 9B:
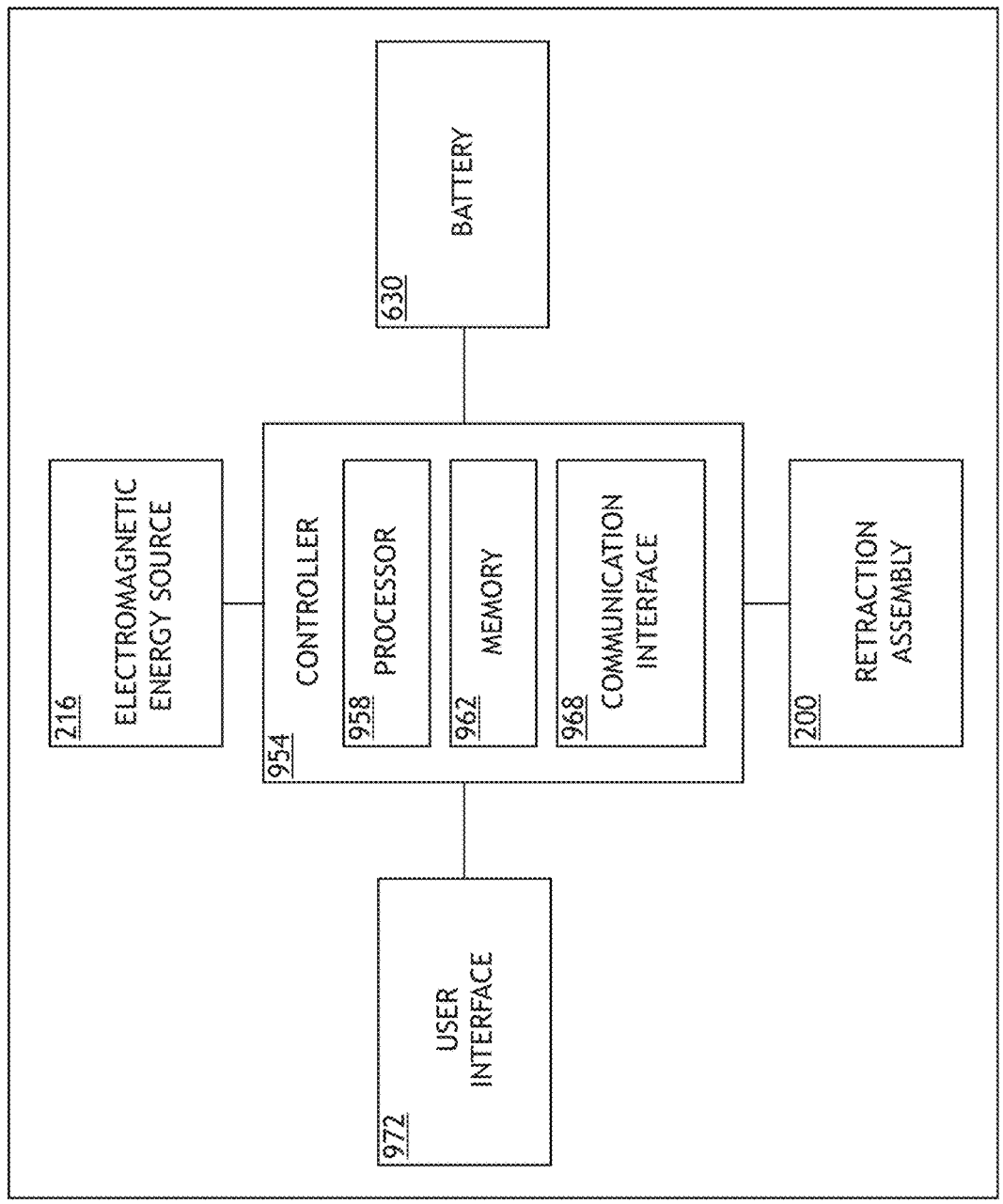
FIG. 9B is a block diagram illustrating an electrical scheme of the self-disinfecting partition system, in accordance with one or more embodiments of the disclosure.

FIG. 9B is a block diagram illustrating an electrical scheme 950 of the self-disinfecting partition system 100, 300, 400, 600, in accordance with one or more embodiments of the disclosure. In embodiments, the electrical scheme 950 includes the battery 630, the one or more electromagnetic energy sources 216, and/or the retraction assembly 200 as described herein. In some embodiments, the electrical scheme 950 further includes a controller 954 configured to provide processing functionality for the self-disinfecting partition system 100, 300, 400, 600, and to interface with componentry within the self-disinfecting partition system 100, 300, 400, 600 including the battery 830, the electromagnetic energy source 216, and the user interface 972. The controller 954 further includes one or more processors 958 (e.g., micro-controllers, circuitry, integrated circuits, field programmable gate arrays (FPGA), or other processing systems), and resident or external memory 962 for storing data, executable code, instructions, and other information. The controller 954 can execute one or more software programs embodied in a non-transitory computer readable medium (e.g., memory 962) that implement techniques described herein (e.g., causing the controller 954 to implement techniques described herein). The controller 954 is not limited by the materials from which it is formed or the processing mechanisms employed therein and, as such, can be implemented via semiconductor(s) and/or transistors (e.g., using electronic integrated circuit (IC) components), and so forth.

The memory 962 can be an example of tangible, computer-readable storage medium that provides storage functionality to store various data and/or program code associated with operation of the controller 954, such as software programs and/or code segments, or other data to instruct the controller 954, and possibly other components of the self-disinfecting partition system 100, 300, 400, 600, to perform the functionality described herein. Thus, the memory 962 can store data, such as a program of instructions for operating the self-disinfecting partition system 100, 300, 400, 600, including its components (e.g., controller 954), and so forth. It should be noted that while a single memory 962 is described, a wide variety of types and combinations of memory 962 (e.g., tangible, non-transitory memory) can be employed. The memory 962 can be integral with the controller 954, can comprise stand-alone memory, or can be a combination of both. Some examples of the memory 962 can include removable and non-removable memory components, such as random-access memory (RAM), read-only memory (ROM), flash memory (e.g., a secure digital (SD) memory card, a mini-SD memory card, and/or a micro-SD memory card), solid-state drive (SSD) memory, magnetic memory, optical memory, universal serial bus (USB) memory devices, hard disk memory, external memory, and so forth.

The controller 954 further includes a communication interface 968. The communication interface 968 can be operatively configured to communicate with components of the self-disinfecting partition system 100, 300, 400, 600. For example, the communication interface 968 can be configured to retrieve data from the controller 954 or other components, transmit data for storage in the memory 962, retrieve data from storage in the memory 962, and so forth. The communication interface 968 can also be communicatively coupled with the controller 954 to facilitate data transfer between components of the self-disinfecting partition system 100, 300, 400, 600. It should be noted that while the communication interface 968 is described as a component of the controller 954, one or more components of the communication interface 968 can be implemented as external components communicatively coupled to the controller 954 via a wired and/or wireless connection.

The electrical scheme 950 further includes a user interface 972 configured communicatively coupled to the controller 954. The user interface 1024 may include any technology that can receive input and/or transmit output to a user including but not limited to switches, button, displays, touch displays, or keyboards. The user interface 972 may also be configured as a wirelines or wireless interface utilizing waveforms including but not limited to wi-fi, Bluetooth, and 5G. For example, a flight attendant may interact with the self-disinfecting partition system 100, 300, 400, 600 via a mobile device (e.g., a smart phone) connected by Bluetooth technology.

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

What is claimed is:

1. A self-disinfecting partition system comprising:
a housing;
an attachment element configured to couple the housing to a seat comprising one or more apertures configured to accept one or more supports;
an extension assembly coupled to the housing and the attachment element, comprising:
the one or more supports coupled to the housing and configured to slide within the one or more apertures, wherein sliding of the one or more supports within the one or more apertures adjusts a distance of the housing from the seat; and
a lock coupled to the attachment element and operationally coupled to the one or more supports and the one or more apertures; wherein the lock is configured upon activation to restrict a movement of the one or more supports relative to the one or more apertures;
a flexible screen configured to block a transmission of microbes, and further configured to deploy from a retracted position within the housing to a deployed position; and
one or more electromagnetic energy sources disposed within the housing configured to emit electromagnetic energy onto the flexible screen when the flexible screen is configured in the retracted position, wherein the electromagnetic energy is configured to disinfect the flexible screen.

2. The self-disinfecting partition system of claim 1, wherein the flexible screen is configured to retract via an accordion fold.

3. The self-disinfecting partition system of claim 1, further comprising an electrical scheme configured to power at least one of the electromagnetic energy source.

4. The self-disinfecting partition system of claim 3, further comprising a user interface communicatively coupled to the electrical scheme.

5. A passenger seat assembly comprising:
a passenger seat; and
a self-disinfecting partition system attached to the passenger seat, comprising:
a housing;
an attachment element configured to couple the housing to the passenger seat comprising one or more apertures configured to accept one or more supports;
an extension assembly coupled to the housing and the attachment element, comprising:
the one or more supports coupled to the housing and configured to slide within the one or more apertures, wherein sliding of the one or more supports within the one or more apertures adjusts a distance of the housing from the seat; and a lock coupled to the attachment element and operationally coupled to the one or more supports and the one or more apertures; wherein the lock is configured upon activation to restrict a movement of the one or more supports relative to the one or more apertures;

a flexible screen configured to block a transmission of microbes, and further configured to deploy from a retracted position within the housing to a deployed position; and one or more electromagnetic energy sources disposed within the housing configured to emit electromagnetic energy onto the flexible screen when the flexible screen is configured in the retracted position, wherein the electromagnetic energy is configured to disinfect the flexible screen.

6. The passenger seat assembly of claim 5, wherein the flexible screen is configured to retract via an accordion fold.

7. The passenger seat assembly of claim 5, wherein the self-disinfecting partition system is attached about a head of the passenger seat, and wherein the flexible screen is configured to deploy in a forward direction away from the headrest.

8. The passenger seat assembly of claim 5, further comprising an electrical scheme configured to power at least one of the electromagnetic energy source.

9. The passenger seat assembly of claim 8, further comprising a user interface communicatively coupled to the electrical scheme.

* * * * *